(12) United States Patent
Duan et al.

(10) Patent No.: US 11,016,389 B2
(45) Date of Patent: May 25, 2021

(54) METHOD OF MAKING HYDROPHOBIC COATING ON CURVED SURFACE SHELL AND ENDOSCOPE

(71) Applicant: Ankon Medical Technologies (Shanghai) Co., LTD., Shanghai (CN)

(72) Inventors: Xiaodong Duan, Pleasanton, CA (US); Meikui Tong, Shanghai (CN)

(73) Assignee: ANKON MEDICAL TECHNOLOGIES (SHANGHAI) CO., LTD, Shanghai (CN)

( * ) Notice: Subject to any disclaimer, the term of this patent is extended or adjusted under 35 U.S.C. 154(b) by 0 days.

(21) Appl. No.: 16/703,118

(22) Filed: Dec. 4, 2019

(65) Prior Publication Data

US 2020/0174371 A1    Jun. 4, 2020

(30) Foreign Application Priority Data

Dec. 4, 2018 (CN) .......................... 201811475514.7

(51) Int. Cl.
| | |
|---|---|
| *B82Y 40/00* | (2011.01) |
| *G03F 7/12* | (2006.01) |
| *B05D 1/02* | (2006.01) |
| *A61B 1/00* | (2006.01) |
| *B29C 59/02* | (2006.01) |
| *B82Y 30/00* | (2011.01) |

(52) U.S. Cl.
CPC .................. *G03F 7/12* (2013.01); *A61B 1/00* (2013.01); *B05D 1/02* (2013.01); *B29C 59/02* (2013.01); *B82Y 30/00* (2013.01); *B82Y 40/00* (2013.01)

(58) Field of Classification Search
None
See application file for complete search history.

(56) References Cited

U.S. PATENT DOCUMENTS

| | | | | |
|---|---|---|---|---|
| 2006/0279025 A1* | 12/2006 | Heidari | ................. | B82Y 10/00 |
| | | | | 264/496 |
| 2007/0141114 A1* | 6/2007 | Muisener | ................. | B05D 7/50 |
| | | | | 424/427 |
| 2007/0158866 A1* | 7/2007 | Wu | ........................ | B82Y 10/00 |
| | | | | 264/1.33 |
| 2009/0194913 A1* | 8/2009 | Chang | ................... | G03F 7/0002 |
| | | | | 264/447 |

(Continued)

FOREIGN PATENT DOCUMENTS

| | | | | |
|---|---|---|---|---|
| CN | 102436141 A | * | 5/2012 | .......... B29C 59/026 |
| CN | 107150465 | | 9/2017 | |
| CN | 108008599 A | * | 5/2018 | |

*Primary Examiner* — Cachet I Proctor
(74) *Attorney, Agent, or Firm* — Treasure IP Group, LLC

(57) ABSTRACT

The present invention provides a method of making a hydrophobic coating on a curved surface shell and an endoscope. The method forms the hydrophobic coating on the curved surface shell through the following steps. A nanoimprint elastic template is provided, and a nanoimprint structure is formed on the nanoimprint elastic template. A curved surface shell is provided, and a nanoimprint adhesive layer is arranged on the curved surface shell. A side where the nanoimprint structure is located in the nanoimprint elastic template and the nanoimprint adhesive layer are bonded together, and the nanoimprint structure is printed on the nanoimprint adhesive layer, and the nanoimprint adhesive layer is cured.

8 Claims, 4 Drawing Sheets

(56) References Cited

U.S. PATENT DOCUMENTS

| | | | |
|---|---|---|---|
| 2010/0065986 A1* | 3/2010 | Nakamura | B82Y 40/00 264/310 |
| 2012/0183690 A1* | 7/2012 | Titulaer | H01L 31/02366 427/256 |
| 2012/0244246 A1* | 9/2012 | Nielsen | B82Y 40/00 425/542 |
| 2013/0091607 A1* | 4/2013 | Gogotsi | B01L 3/021 850/60 |
| 2015/0380140 A1* | 12/2015 | Duan | A61B 1/041 600/109 |
| 2016/0287058 A1* | 10/2016 | Ye | A61B 1/126 |
| 2017/0271381 A1* | 9/2017 | Sone | H01L 27/1288 |
| 2018/0066131 A1* | 3/2018 | Jin | C08J 9/228 |

* cited by examiner

METHOD OF MAKING HYDROPHOBIC COATING ON CURVED SURFACE SHELL AND ENDOSCOPE

CROSS-REFERENCE OF RELATED APPLICATIONS

The application claims priority to Chinese Patent Application No. 201811475514.7 filed on Dec. 4, 2018, the contents of which are incorporated by reference herein.

FIELD OF INVENTION

The present invention relates to surface treatment field, and more particularly to a method of making hydrophobic coating on curved surface shell and an endoscope having the curved surface shell.

BACKGROUND

During use, an endoscope can be in close contact with human body fluids, including blood, tissue fluid, saliva, gastric juice, etc. These fluids contain a plurality of viscous substances that can be easily stained on the camera lens surface and affect imaging. The current method is to add a spray gun to the endoscope to clean the surface of lens with spraying of water. However, use of a spray gun is impossible in some application scenarios, such as in a capsule endoscope. Therefore, it is particularly important to prepare a stable hydrophobic coating on the surface of endoscope lens. Existing hydrophobic coatings are typically arranged to make a nanostructure on the surface of an endoscope lens.

In prior art, the nanostructured hydrophobic coating is generally formed by means of lithography, spraying of nanoparticles or plasma bombardment. However, in order to facilitate the movement of the endoscope inside human body, the surface of the endoscope is typically a curved surface on a plastic shell, or a capsule endoscope is directly used. However, the lithography method cannot make a nanostructure on the curved surface, and the method of plasma bombardment is costly and has less efficiency. In addition, when the method of spraying nanoparticles is used, the plastic shell cannot withstand the high temperature in the process.

SUMMARY OF THE INVENTION

The present invention provides a method of making hydrophobic coating on a curved surface shell and an endoscope produced by the method. The method can easily form a hydrophobic coating on a curved surface shell of the endoscope.

The present invention provides a method of making a hydrophobic coating on a curved surface shell, comprising the following steps:
providing a nanoimprint elastic template, wherein a nanoimprint structure is formed on the nanoimprint elastic template;
providing a curved surface shell, wherein a nanoimprint adhesive layer is arranged on the curved surface shell;
bonding a side where the nanoimprint structure is located in the nanoimprint elastic template and the nanoimprint adhesive layer together, and printing the nanoimprint structure on the nanoimprint adhesive layer; and
curing the nanoimprint adhesive layer.

Further, the nanoimprint adhesive layer is cured by heating or ultraviolet irradiation.

Further, the nanoimprint structure is a nano-conical structure, a nano-cylindrical structure, a rectangular pyramid structure or a triangular prism structure.

Further, the thickness of the nanoimprint adhesive layer is a value selected from 100 nm-5000 nm.

Further, the method further comprises forming a plurality of nanoparticles on the nanostructure of the nanoimprint adhesive layer after the nanoimprint adhesive layer is cured.

Further, the nanoparticles are formed on the nanostructure of the nanoimprint adhesive layer by evaporation or spraying.

Further, the nanoparticles are fluoride.

Further, in the step that the side where the nanoimprint structure is located in the nanoimprint elastic template and the nanoimprint adhesive layer are bonded together, and the nanoimprint structure is printed on the nanoimprint adhesive layer, the method further comprises the following steps:
placing the side where the nanoimprint structure is located in the nanoimprint elastic template on the nanoimprint adhesive layer to form a nanoimprint assembly;
putting the nanoimprint assembly in a sealed working chamber;
providing a flexible transparent cover film, covering the flexible transparent cover film on the nanoimprint assembly and extending over the edges of the nanoimprint assembly to contact the bottom plate of the sealed working chamber, so as to form an accommodating cavity between the flexible transparent cover film and the bottom plate of the sealed working chamber to accommodate the nanoimprint assembly;
reducing air pressure in the sealed working chamber such that the air pressure in the accommodating cavity is lower than the air pressure in the sealed working chamber in an initial state; and
increasing air pressure in the sealed working chamber such that the air pressure in the sealed working chamber is higher than the air pressure in the accommodating cavity.

Further, the method further comprises forming a flexible substrate film on the bottom plate of the sealed working chamber, and covering the flexible transparent cover film on the nanoimprint assembly and extending over the edges of the nanoimprint to contact the flexible substrate film.

The present invention also provides an endoscope made by the method of making a hydrophobic coating on a curved surface shell as disclosed herein.

In summary, the present invention, by providing a nanoimprint elastic template with a nanoimprint structure and coating a nanoimprint adhesive layer on a curved surface shell, makes it possible to print a nanoimprint structure on a nanoimprint elastic template onto a nanoimprint adhesive layer and then cure the nanoimprint adhesive layer to form a nanostructure on a curved surface shell. The nanostructure has a good hydrophobic effect and can effectively prevent adhesion of various mucus in human body. Since a nanoimprint elastic template is used, and the nanoimprint elastic template can be bent to fit with the curvature of the curved surface shell of an endoscope for a better imprinting of a nanoimprint structure, by the method, a hydrophobic coating can be easily made on the curved surface shell of the endoscope. Further, the present invention, by an arrangement of sealed working chamber and flexible transparent cover film, can bond the nanoimprint elastic template to the nanoimprint adhesive layer under a low pressure, and can also uniformly apply pressure to the nanoimprint assembly. This method can reduce the time taken for imprinting and thereby increase work efficiency.

The above description is only an overview of the technical solutions of the invention. For a thorough understanding of the technical means of the invention, and implementation in accordance with the specification, and that the above-described and other objects, features and advantages of the invention can be more clearly understood, detailed description of the preferred embodiments can be described in detail with reference to the accompanying drawings.

DETAILED DESCRIPTION

The present invention can be described in detail below with reference to the accompanying drawings and preferred embodiments.

The present invention provides a method of making hydrophobic coating on a curved surface shell and an endoscope produced by the method. The method can easily form a hydrophobic coating on a curved surface shell of the endoscope.

Figure 1:
FIG. 1 is a structural view showing the first embodiment of a nanoimprint elastic template according to the present invention.
Figure 2:
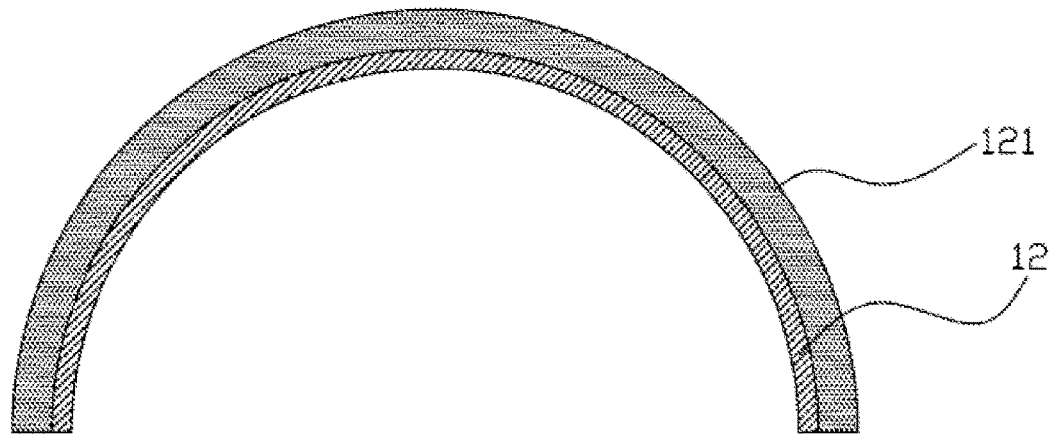
FIG. 2 is a structural view showing the first embodiment of a curved surface shell according to the present invention.
Figure 3:
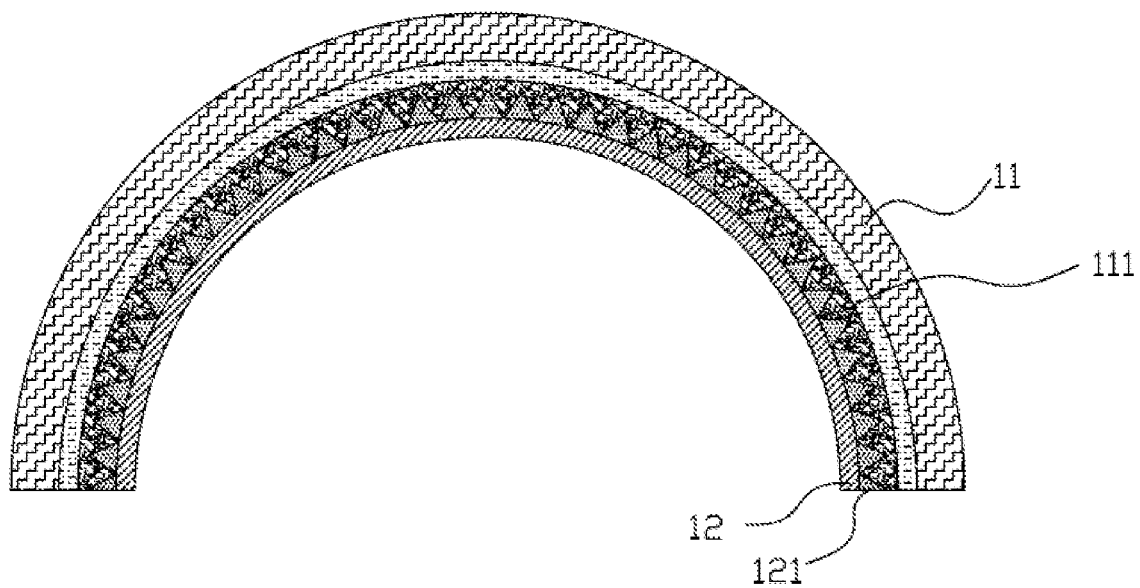
FIG. 3 is a structural view showing the first embodiment of printing a nanoimprint structure according to the present invention.
Figure 4:
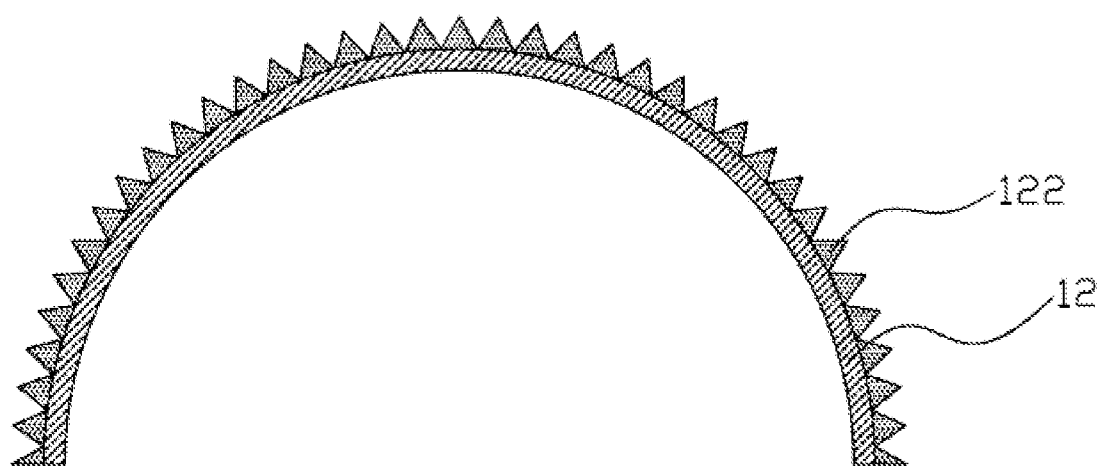
FIG. 4 is a structural view showing the first embodiment of forming a hydrophobic coating on a curved surface shell according to the present invention.

FIG. 1 is a structural view showing the first embodiment of a nanoimprint elastic template according to the present invention. FIG. 2 is a structural view showing the first embodiment of a curved surface shell according to the present invention. FIG. 3 is a structural view showing the first embodiment of printing a nanoimprint structure according to the present invention, and FIG. 4 is a structural view showing the first embodiment of forming a hydrophobic coating on a curved surface shell according to the present invention. Referring to FIGS. 1-4, the present invention provides a method of making a hydrophobic coating on a curved surface shell, comprising the following steps:

a nanoimprint elastic template 11 is provided, and a nanoimprint structure 111 is formed on the nanoimprint elastic template 11;

a curved surface shell 12 is provided, and a nanoimprint adhesive layer 121 is arranged on the curved surface shell 12;

a side where the nanoimprint structure 111 is located in the nanoimprint elastic template 11 and the nanoimprint adhesive layer 121 are bonded together, and the nanoimprint structure 111 is printed on the nanoimprint adhesive layer 121; and the nanoimprint adhesive layer 121 is cured.

As the nanoimprint elastic template 11 is separated from the curved surface shell 12, the nanoimprint structure 111 on the nanoimprint elastic template 11 is printed onto the nanoimprint adhesive layer 121 of the curved surface shell 12, and the "printed" nanostructure 122 is formed on the curved surface shell 12. That is, a hydrophobic coating is formed on the curved surface shell 12.

The curved surface shell 12 can be any curved surface shell that requires a hydrophobic surface, such as a curved surface shell of an endoscope.

In the embodiment, the hydrophobic coating is formed by a nanostructure 122. By providing a nanoimprint elastic template 11 with a nanoimprint structure 111 and coating a nanoimprint adhesive layer 121 on a curved surface shell 12, it can print the nanoimprint structure 111 on the nanoimprint elastic template 11 onto the nanoimprint adhesive layer 121 and then cure the nanoimprint adhesive layer 121 to form a nanostructure 122 on a curved surface shell 12. The nanostructure 122 has a good hydrophobic effect and can effectively prevent adhesion of various mucus in human body. Since a nanoimprint elastic template 11 is used, and the nanoimprint elastic template 11 can be bent to fit with the curvature of the curved surface shell of an endoscope for a better imprinting of a nanoimprint structure 111, a hydrophobic coating can be easily made on the curved surface shell of the endoscope.

In the embodiment, the thickness of the nanoimprint adhesive layer 121 can be a value selected from 100 nm to 5000 nm. The nanoimprint adhesive 121 can be a thermal curing nanoimprint adhesive such as PDMS (polydimethylsiloxane), PMMA (polymethyl methacrylate), etc., and correspondingly, the nanoimprint structure 111 in the nanoimprint adhesive layer 121 is cured by heating. In other embodiments, the nanoimprint adhesive may also be an ultraviolet curing nanoimprint adhesive, such as I-UVP light curing adhesive, NXR-2000 series light curing adhesive, and NXR-4000 series light curing adhesive, etc., and correspondingly, the nanoimprint structure 111 in the nanoimprint adhesive layer 121 is cured by UV irradiating.

In the embodiment, the curved surface shell 12 may be made of glass, quartz, plastic or the like.

In the embodiment, the nanoimprint structure 111 on the nanoimprint elastic template 11 can be, but not limited to, a nano-conical structure, a nano-cylindrical structure, a rectangular pyramid structure or a triangular prism structure.

Figure 5:
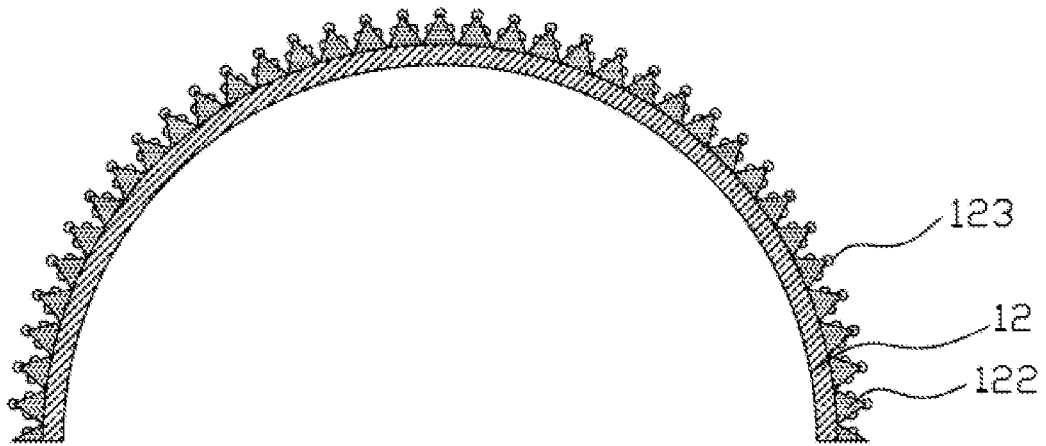
FIG. 5 is a structural view showing the second embodiment of forming a hydrophobic coating on a curved surface shell according to the present invention.

FIG. 5 is a structural view showing the second embodiment of forming a hydrophobic coating on a curved surface shell according to the present invention. Referring to FIG. 5, the method of making a hydrophobic coating on a curved surface shell provided in the second embodiment is basically the same as that provided in the first embodiment. The difference lies in that, in the embodiment, after the nanoimprint adhesive layer 121 is cured, that is, after the nanostructure 122 is formed on the curved surface shell 12, a plurality of nanoparticles 123 are formed on the nanostructure 122. The nanoparticles 123 may be fluorides formed on the surface of the nanoimprint structure 111 by evaporation or spraying. Surface energy of the nanostructure 122 can be reduced by the nanoparticles 123, so that the hydrophobic effect can be further improved by dual action of the nanostructure 122 and the nanoparticles 123.

Figure 6:
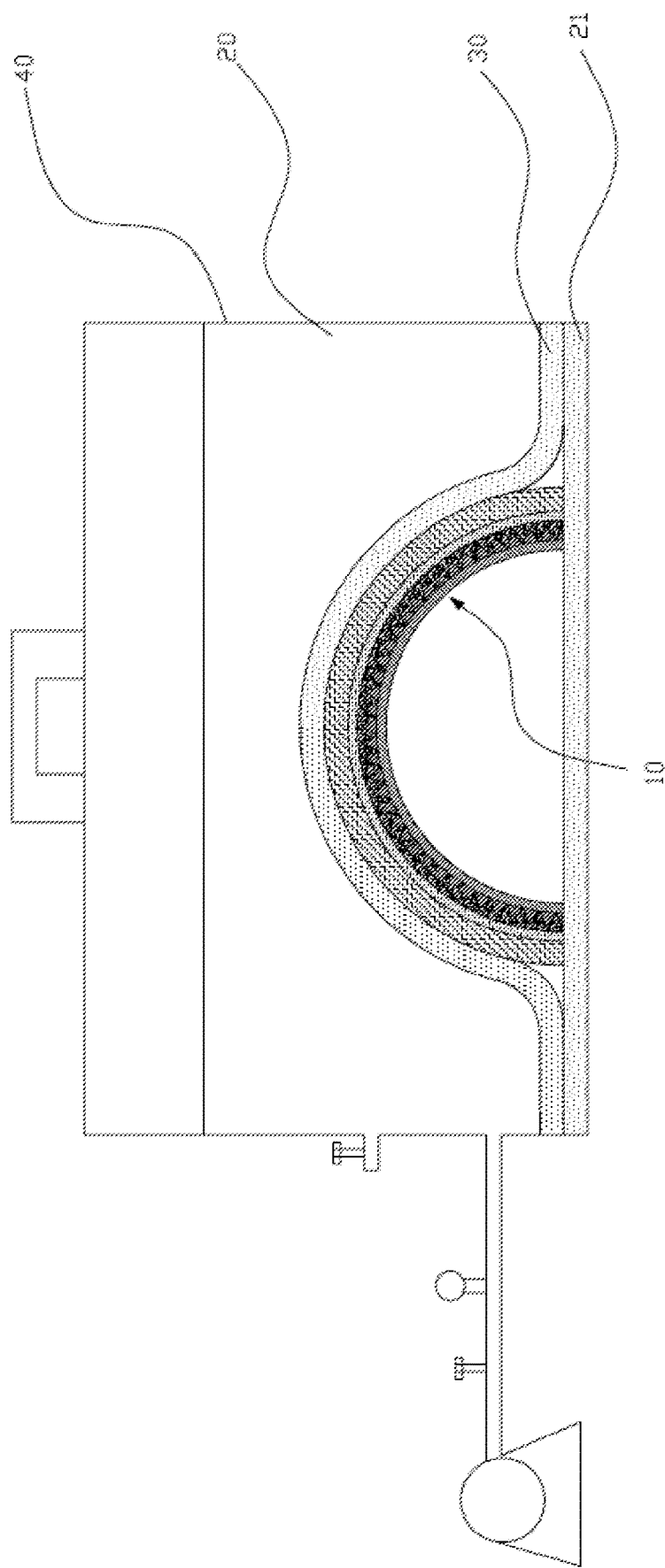
FIG. 6 is a structural view showing the third embodiment of printing a nanoimprint structure according to the present invention.

Referring to FIG. 6, a structural view showing a third embodiment of printing a nanostructure according to the present invention. The method of making a hydrophobic coating on a curved surface shell according to the third embodiment is basically the same as that according to the first embodiment. The difference lies in that when bonding a side where the nanoimprint structure 111 is located in the nanoimprint elastic template to the nanoimprint adhesive layer 121 and printing the nanoimprint structure 111 onto the nanoimprint adhesive layer 121, the method further comprises the following steps:

placing the side where the nanoimprint structure 111 is located in the nanoimprint elastic template 11 on the nanoimprint adhesive layer 121 to form a nanoimprint assembly 10;

putting the nanoimprint assembly 10 in a sealed working chamber 20;

providing a flexible transparent cover film 30, covering the flexible transparent cover film 30 on the nanoimprint assembly 10 and extending over the edges of the nanoimprint assembly 10 to contact the bottom plate of the sealed working chamber 20, so as to form an accommodating cavity 40 between the flexible transparent cover film 30 and the bottom plate of the sealed working chamber 20 to accommodate the nanoimprint assembly 10;

reducing air pressure in the sealed working chamber 20 such that the air pressure in the accommodating cavity 40 is lower than the air pressure in the sealed working chamber 20 in an initial state, that is the original air pressure in the sealed working chamber 20 before reduction; and increasing air pressure in the sealed working chamber 20 such that the air pressure in the sealed working chamber 20 is higher than the air pressure in the accommodating cavity 40. By this method, the nanoimprint elastic template 11 is bonded to the nanoimprint adhesive layer 121 and the nanoimprint structure 111 is printed onto the nanoimprint adhesive layer 121.

In the embodiment, a flexible transparent cover film 30 is covered on the nanoimprint assembly 10, and the flexible transparent cover film 30 extends over the edges of the nanoimprint assembly 10 to contact the bottom plate of the sealed working chamber 20. Then, an accommodating cavity 40 is formed between the flexible transparent cover film 30 and the bottom plate of the sealed working chamber 20 to accommodate the nanoimprint assembly 10. First of all, reduce the air pressure in the sealed working chamber 20 with a vacuum pump. Since the flexible transparent cover film 30 is just in a contact state with the bottom plate of the sealed working chamber 20, when the air pressure in the sealed working chamber 20 is reduced, the air in the accommodating cavity 40 can overflow, and the air pressure in the accommodating chamber 40 can be lower than its initial state, that is the original air pressure in the sealed working chamber before reduction (but may be higher than the air pressure in the sealed working chamber 20 at this time). Second, increase the air pressure in the sealed working chamber 20. Since at this time the air pressure outside the accommodating cavity 40 can compress the flexible transparent cover film 30 to make it have a tighter contact with the bottom plate and disable the air in the sealed working chamber 20 to enter the accommodating cavity 40, the air pressure in the sealed working chamber 20 can be higher than the air pressure in the accommodating cavity 40, and the flexible transparent cover film 30 which can transmit the pressure of air in the sealed working chamber 20 applies force to the nanoimprint assembly 10.

When the nanoimprint elastic template 11 is placed on the nanoimprint adhesive layer 121 in an unbent shape, the nanoimprint elastic template 11 can be bent under the action of the flexible transparent cover film 30, and then bonded to the nanoimprint adhesive layer 121, and the nanoimprint structure 111 is printed on the nanoimprint adhesive layer 121. It can be understood that the nanoimprint elastic template 11 can also be bonded to the nanoimprint adhesive layer 121 in advance. The method enables the nanoimprint elastic template 11 to be better bonded to the nanoimprint adhesive layer 121 according to the outer shape of the curved surface shell 12 of an endoscope and applies uniform force to the nanoimprint assembly 10, so that it is easier to shape the nanostructure 122.

In the process, it is no longer necessary to inject high-pressure gas into the sealed working chamber 20, and it is no longer necessary to add a pressure boosting device to complete the bonding process. Further, after bonding, the method can directly cure the nanoimprint adhesive layer 121, which can shorten the time required for imprinting and improve work efficiency.

Further, the method further comprises: forming a flexible substrate film 21 on the bottom plate of the sealed working chamber 20, covering the flexible transparent cover film 30 on the nanoimprint assembly 10 and extending over the edges of the nanoimprint assembly 10 to contact the flexible substrate film 21. By the arrangement of the flexible substrate film 21, the flexible transparent cover film 30 can have a tighter contact with the bottom plate of the sealed working chamber 20 under the action of external pressure.

Further, in the step of reducing air pressure in the sealed working chamber 20, a vacuum pump can be used to pump air out of the sealed working chamber to reduce the air pressure therein to 5 Pa~100 Pa.

Further, in the step of increasing air pressure in the sealed working chamber 20, the inside of the sealed working chamber 20 is in communication with the outside. That is, the air pressure in the sealed working chamber 20 is substantially equal to the atmospheric pressure at this time.

In summary, the present invention, by providing a nanoimprint elastic template 11 with a nanoimprint structure 111 and coating a nanoimprint adhesive layer 121 on a curved surface shell 12, makes it possible to print a nanoimprint structure 111 on a nanoimprint elastic template 11 onto a nanoimprint adhesive layer 121 and then cure the nanoimprint adhesive layer 121 to form a nanostructure 122 on a curved surface shell 12. The nanostructure 122 has a good hydrophobic effect and can effectively prevent adhesion of various mucus in human body. Since a nanoimprint elastic template 11 is used, and the nanoimprint elastic template 11 can be bent to fit with the curvature of the curved surface shell 12 of an endoscope for a better imprinting of a nanoimprint structure 111. By the method, a hydrophobic coating can be easily made on the curved surface shell 12. Further, the present invention, by an arrangement of the sealed working chamber 20 and the flexible transparent cover film 30, can bond the nanoimprint elastic template 11 to the nanoimprint adhesive layer 121 under a low pressure, and can also uniformly apply pressure to the nanoimprint assembly 10. The method can reduce the time taken for imprinting and thereby increase work efficiency.

The present invention also provides an endoscope of which the curved surface shell have a hydrophobic coating 122 made by the method of making a hydrophobic coating 122 on a curved surface shell as disclosed herein. For other technical features of the endoscope, please refer to the prior art, and details are not described herein.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A method of making a hydrophobic coating on a curved surface shell of a capsule endoscope, comprising the following steps:
   providing a nanoimprint elastic template, wherein a nanoimprint template structure is formed on the nanoimprint elastic template;
   providing a curved surface shell, wherein a nanoimprint adhesive layer is arranged on the curved surface shell;
   binding the nanoimprint elastic template with the curved surface shell on a side where the nanoimprint template structure is located in the nanoimprint elastic template and where the nanoimprint adhesive layer is located, and printing the nanoimprint template structure onto the nanoimprint adhesive layer, by the steps of
      forming a nanoimprint assembly by placing the side where the nanoimprint structure is located in the nanoimprint elastic template on the nanoimprint adhesive layer;
      putting the nanoimprint assembly in a sealed working chamber;
      providing a flexible transparent cover film,
      covering the flexible transparent cover film on the nanoimprint assembly,
      extending over the edges of the nanoimprint assembly,
      and providing drape portion of the flexible transparent cover film extend horizontally, to removably and conformally supported by a flexible bottom plate of the sealed working chamber and forming a releasable surface area contact, so as to form an accommodating cavity between the flexible transparent cover film and the bottom plate of the sealed working chamber to accommodate the nanoimprint assembly;
   reducing air pressure in the sealed working chamber such that air pressure in the accommodating cavity is lower than the air pressure in the sealed working chamber in an initial state; and
   increasing air pressure in the sealed working chamber such that the air pressure in the sealed working chamber is higher than the air pressure in the accommodating cavity; and
   curing the nanoimprint adhesive layer to obtain the hydrophobic coating, which is a nanostructure printed on the nanoimprint adhesive layer of the curved surface shell.

2. The method of claim 1, wherein the nanoimprint adhesive layer is cured by heating or ultraviolet irradiation.

3. The method of claim 1, wherein the nanoimprint structure is a nano-conical structure, a nano-cylindrical structure, a rectangular pyramid structure or a triangular prism structure.

4. The method of claim 1, wherein the thickness of the nanoimprint adhesive layer is a value selected from 100 nm-5000 nm.

5. The method of claim 1, further comprising:
   forming a plurality of nanoparticles on the nanostructure of the nanoimprint adhesive layer after the nanoimprint adhesive layer is cured.

6. The method of claim 5, wherein the nanoparticles are formed on the nanostructure of the nanoimprint adhesive layer by evaporation or spraying.

7. The method of claim 5, wherein the nanoparticles are fluoride.

8. The method of claim 1, wherein the step of reducing air pressure in the sealed working chamber further comprising reducing air pressure in the sealed working chamber to 5 Pa to 100 Pa.

* * * * *